United States Patent [19]

Ghosh et al.

[11] 4,096,265
[45] Jun. 20, 1978

[54] BENZOPYRANO[3,4-d]PYRIDINE-2-CYANO, CARBOXAMIDOXIMES AND CARBOXIMIDATES

[75] Inventors: Anil Chandra Ghosh, Lexington; Raj Kumar Razdan, Belmont, both of Mass.

[73] Assignee: Sharps Associates, Cambridge, Mass.

[21] Appl. No.: 739,546

[22] Filed: Nov. 8, 1976

[51] Int. Cl.² .................. C07D 491/04; A61K 31/44
[52] U.S. Cl. ............................. 424/256; 260/296 H
[58] Field of Search ................... 260/296 H, 294.9; 424/256, 263

[56] References Cited

U.S. PATENT DOCUMENTS 3,535,327 10/1970 Pars et al. .................. 260/294.9

OTHER PUBLICATIONS

International Union of Pure and Applied Chemistry, Nomenclature of Organic Chemistry, Definitive Rules for Section A, Hydrocarbons Section B, Fundamental Heterocyclic Systems etc. pp. 25-26, London, Butterworths Scientific Publications, 1958.
Patterson et al., The Ring Index 2nd ed. pp. 1271-1272, American Chemical Society, 1960.
Chemical Abstracts, Eighth Collective Index, vols. 66-75, 1967-1971, Subjects Benzimidazolin-By p. 4369S.
Harris et al., Chem. Abst. 1973, vol. 79, No. 92191v.
Harris et al., Chem. Abst., 1974, vol. 80, No. 63863f.

Pars et al., J. Amer. Chem. Soc., 1966, vol. 88, pp. 3664-3665.
Sterling Drug Chem. Abst., 1970, vol. 72, 66922v.

Primary Examiner—Natalie Trousof
Attorney, Agent, or Firm—Merriam, Marshall & Bicknell

[57] ABSTRACT

Benzopyrano[3,4-d]pyridine-2-cyano, carboxamidoximes and carboximidates of the formula

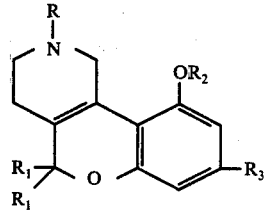

wherein R represents $-C \equiv N$,

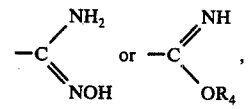

$R_1$ is a lower alkyl, $R_2$ is hydrogen or a lower alkyl and $R_3$ is a straight or branched alkyl having 1 to 20 carbons, a cycloalkyl-lower alkyl group in which the cycloalkyl group has 3 to 8 carbons or it is an arylalkyl group, and $R_4$ is a lower alkyl group.

The compounds are useful for lowering blood pressure.

18 Claims, No Drawings

BENZOPYRANO[3,4-d]PYRIDINE-2-CYANO, CARBOXAMIDOXIMES AND CARBOXIMIDATES

This invention relates to 5,5-di-lower alkyl-8-alkyl, cycloalkyl-lower alkyl or arylalkyl-10-hydroxy-1,2,3,4-tetrahydro-5H-[1]benzopyrano[3,4-d]pyridines. More particularly, this invention is concerned with novel 2-substituted derivatives of those and 10-alkoxy compounds, processes of producing such compounds, intermediates produced in such processes, and the pharmacological activities of the compounds.

According to the present invention there is provided novel 2-substituted-5,5-di-lower alkyl-8-alkyl, cycloalkyl-lower alkyl or arylalkyl-10-hydroxy or lower alkoxy-1,2,3,4-tetrahydro-5H-[1]benzopyrano[3,4-d]pyridines of the formula

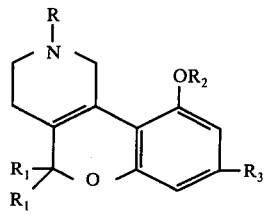

wherein R represents -C≡N (cyano),

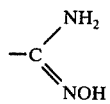

(carboxamidoxime) or

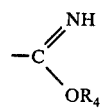

(carboximidate), $R_1$ is a lower alkyl such as those having 1 to 6 carbons including methyl, ethyl and propyl, $R_2$ is hydrogen or a lower alkyl group having 1 to 6 carbons including methyl, ethyl and propyl and $R_3$ is an alkyl which is straight chained or branched such as those having 1 to 20 carbons including methyl, ethyl, amyl, hexyl, 2-heptyl, n-heptyl, 1,2-dimethylheptyl, 1,1-dimethylheptyl, n-octyl, 2-nonyl, 2-tetradecyl, n-hexadecyl and 2-eicosanyl, or $R_3$ is a cycloalkyl-lower alkyl group in which the cycloalkyl group has 3 to 8 carbons and the lower alkyl group has 1 to 6 carbons, including the cyclopropylmethyl, cyclopentylethyl, cyclohexylpropyl and cyclooctylbutyl groups, or $R_3$ is an aryl-$C_1$ to $C_{10}$-alkyl group and particularly phenyl-alkyl groups such as benzyl, phenylethyl, phenylpropyl, 4-(4-fluorophenyl)-1-methylbutyl, 4-(4-methylphenyl)-1-methylbutyl and 1,2-dimethyl-7-phenylheptyl and $R_4$ is a lower alkyl group having 1 to 6 carbons such as methyl, ethyl and propyl. It is intended to include in phenyl-alkyl groups those groups in which the phenyl has 1 to 3 halo groups such as chloro, bromo and fluoro, hydroxy, lower alkoxy groups such as methoxy, ethoxy and propoxy, nitro and lower alkyl groups such as methyl, ethyl and propyl, and trifluoromethyl. Compounds included within the above formula are those in which:

1. R is -C≡N, $R_1$ is methyl and $R_2$ is hydrogen or methyl.
2. R is

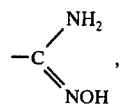

$R_1$ is methyl and $R_2$ is hydrogen or methyl.

3. R is

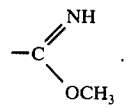

4. R is

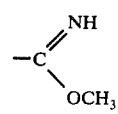

and $R_1$ is methyl.

5. R is

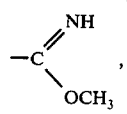

$R_1$ is methyl and $R_2$ is hydrogen or methyl. The nomenclature used in this specification to identify the compounds is the same as that used in many U.S. Pat., as see Nos. 3,991,194; 3,878,219; 3,798,326; 3,787,424; 3,656,906; 3,576,798 and 3,522,260. The current Chemical Abstracts nomenclature, however, differs from that used in this specification. Chemical Abstracts names the ring system

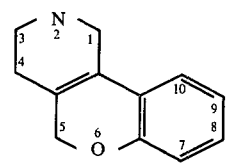

as 1,3,4,5-tetrahydro-2H-[1] benzopyrano[4,3-c]-pyridine. If that nomenclature were followed the compound of Example 1 would be named 2-Cyano-5,5-dimethyl-8-(1,2-dimethylheptyl)-1,3,4,5-tetrahydro-2H-[1]benzopyrano[4,3-c]pyridine-10-ol and the compound of Example 2 would be named 5,5-dimethyl-8-(1,2-dimethylheptyl)-1,3,4,5-tetrahydro-2H-[1]benzopyrano[4,3-c]pyridine-10-ol-2-carboxamidoxime.

In the first step of producing the compounds of this invention a previously known (see U.S. Pat. Nos. 3,576,798 and 3,932,432) 5,5-di-lower alkyl-8-alkyl, cycloalkyl-lower alkyl or arylalkyl-10-hydroxy-1,2,3,4-tetrahydro-5H-[1] benzopyrano[3,4-d]pyridine is reacted with a reactive cyanogen halide, such as cyanogen bromide, to produce a 2-cyano-5,5-di-lower alkyl-8-alkyl, cycloalkyl-lower alkyl or arylalkyl-10-hydroxy-1,2,3,4-tetrahydro-5H-[1]benzopyrano[3,4-d]pyridine. This process step may be illustrated as follows:

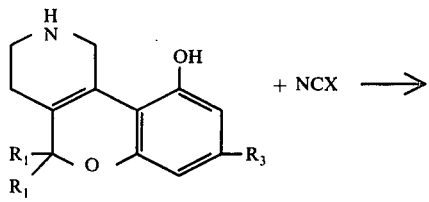

+ NCX ⟶

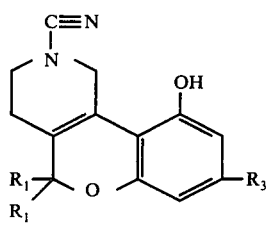

wherein R₁ and R₃ have the previously assigned meaning and X is a reactive halo ion and particularly is bromo or chloro.

The described reaction is readily effected by combining the reactants in a suitable liquid reaction medium and advisably a medium in which the reactants are soluble, such as a lower alcohol like methanol. The reaction proceeds to completion in a few hours or less at a temperature from about 0° to 30° C. Following termination of the reaction the desired product can be readily isolated from the reaction mixture by conventional separation procedures.

Some of the 2-cyano derivatives which are produced as described are 2-cyano-5,5-dimethyl-8-(1,2-dimethylheptyl)-10-hydroxy-1,2,3,4-tetrahydro-5H-[1]benzopyrano[3,4-d]pyridine, 2-cyano-5,5-dimethyl-8-(2-heptyl)-10-hydroxy-1,2,3,4-tetrahydro-5H-[1]benzopyrano[3,4-d]pyridine, 2-cyano-5,5-dimethyl-10-hydroxy-8-(1-pentyl)-1,2,3,4-tetrahydro-5H-[1]benzopyrano [3,4-d]pyridine, 2-cyano-8-(1-cyclohexylethyl)-5,5-dimethyl-10-hydroxy-1,2,3,4-tetrahydro-5H-[1]benzopyrano[3,4-d]pyridine, 2-cyano-8-(3-cyclopentylpropyl)-5,5-dimethyl-10-hydroxy-1,2,3,4-tetrahydro-5H-[1]benzopyrano[3,4-d]pyridine, 2-cyano-5,5-dimethyl-8-[4-(4-fluorophenyl)-1-methylbutyl]-10-hydroxy-1,2,3,4-tetrahydro-5H-[1]benzopyrano[3,4-d]pyridine, 2-cyano-5,5-dimethyl-8-[4-(4-methylphenyl)-1-methylbutyl]-10-hydroxy-1,2,3,4-tetrahydro-5H-[1]benzopyrano[3,4-d]pyridine and 2-cyano-5,5-dimethyl-8-(1,2-dimethyl-7-phenylheptyl)-10-hydroxy-1,2,3,4-tetrahydro-5H-[1]benzopyrano[3,4-d]pyridine.

The 2-cyano-5,5-di-lower alkyl-8-alkyl, cycloalkyl-lower alkyl or arylalkyl-10-hydroxy-1,2,3,4-tetrahydro-5H-[1]benzopyrano[3,4-d]pyridines can be readily etherified or converted to the otherwise corresponding 10-lower alkoxy compound by reacting the 10-hydroxy compound with a reactive halo lower alkane such as iodomethane, bromoethane or iodopropane. The reaction is readily effected by combining the reactants in an anhydrous liquid reaction medium such as acetone in the presence of a hydrohalide binding material, such as sodium carbonate. An elevated temperature, such as the reflux temperature, serves to promote the reaction and bring it to completion more quickly. Following the reaction the desired product can be isolated from the reaction mixture by conventional procedures.

Among the ethers which can be produced as described are 2-cyano-5,5-dimethyl-8-(1,2-dimethylheptyl)-10-methoxy-1,2,3,4-tetrahydro-5H-[1]benzopyrano[3,4-d]pyridine, 2-cyano-5,5-dimethyl-10-ethoxy-8-(2-heptyl)-1,2,3,4-tetrahydro-5H-[1]benzopyrano[3,4-d]pyridine, 2-cyano-5,5-dimethyl-8-(1-pentyl)-10-propoxy-1,2,3,4-tetrahydro-5H-[1]benzopyrano [3,4-d]pyridine, 2-cyano-10-butoxy-8-(1-cyclohexylethyl)-5,5-dimethyl-1,2,3,4-tetrahydro-5H-[1]benzopyrano[3,4-d] pyridine, 2-cyano-8-(3-cyclopentylpropyl)-5,5-dimethyl-10-pentoxy-1,2,3,4-tetrahydro-5H-[1]benzopyrano[3,4-d]pyridine, 2-cyano-5,5-dimethyl-8-[4-(4-fluorophenyl)-1-methylbutyl]-10-methoxy-1,2,3,4-tetrahydro-5H-[1]benzopyrano[3,4-d]pyridine, 2-cyano-5,5-dimethyl-10-ethoxy-8-[4-(4-methylphenyl)-1-methylbutyl]-1,2,3,4-tetrahydro-5H-[1]benzopyrano[3,4-d] pyridine and 2-cyano-5,5-dimethyl-8-(1,2-dimethyl-7-phenyl-heptyl)-10-propoxy-1,2,3,4-tetrahydro-5H-[1]benzopyrano[3,4-d]pyridine.

The already described 2-cyano compounds, whether they have a 10-hydroxy or 10-lower alkoxy substituent, can be converted to the otherwise corresponding 2-carboxamidoximes by reaction with hydroxylamine in a suitable liquid reaction medium, such as dimethylformamide, at a moderately elevated temperature. The process can be illustrated as follows:

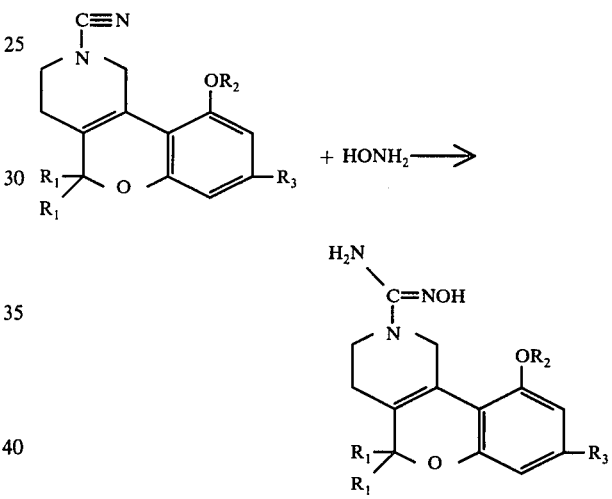

wherein R₁, R₂ and R₃ have the previously assigned significance. The reaction proceeds to essential completion in 1 to 2 hours after which the product can be separated from the reaction mixture.

Among the compounds produced in the described manner are 5,5-dimethyl-8-(1,2-dimethylheptyl)-10-hydroxy-1,2,3,4-tetrahydro-5H-[1]benzopyrano[3,4-d]pyridine-2-carboxamidoxime, 5,5-dimethyl-8-(2-heptyl)-10-hydroxy-1,2,3,4-tetrahydro-5H-[1]benzopyrano[3,4-d]pyridine-2-carboxamidoxime, 5,5-dimethyl-10-hydroxy-8-(1-pentyl)-1,2,3,4-tetrahydro-5H-[1]benzopyrano[3,4-d]pyridine-2-carboxamidoxime, 8-(1-cyclohexylethyl)-5,5-dimethyl-10-hydroxy-1,2,3,4-tetrahydro-5H-[1]benzopyrano[3,4-d]pyridine-2-carboxamidoxime, 8-(3-cyclopentylpropyl)-5,5-dimethyl-10-hydroxy-1,2,3,4-tetrahydro-5H-[1]benzopyrano[3,4-d]pyridine-2-carboxamidoxime, 5,5-dimethyl-8-[4-(4-fluorophenyl)-1-methylbutyl]-10-hydroxy-1,2,3,4-tetrahydro-5H-[1]benzopyrano [3,4-d]pyridine-2-carboxamidoxime, 5,5-dimethyl-8-[4-(4-methylphenyl)-1-methylbutyl]-10-hydroxy-1,2,3,4-tetrahydro-5H-[1]benzopyrano[3,4-d]pyridine-2-carboxamidoxime and 5,5-dimethyl-8-(1,2-dimethyl-7-phenylheptyl)-10-hydroxy-1,2,3,4-tetrahydro-5H-[1]benzopyrano[3,4-d]pyridine-2-carboxamidoxime and the corresponding compounds in which a 10-methoxy, ethoxy, propoxy, butoxy or pentoxy group is present in place of the 10-hydroxy group.

The 2-cyano-5,5-di-lower alkyl-8-alkyl, cycloalkyl-lower alkyl or arylalkyl-10-hydroxy or lower alkoxy-1,2,3,4-tetrahydro-5H-[1]benzopyrano[3,4-d]pyridines upon reaction with an alkali metal lower alkoxide yield the otherwise corresponding lower alkyl 2-carboximidates. This process can be represented as follows:

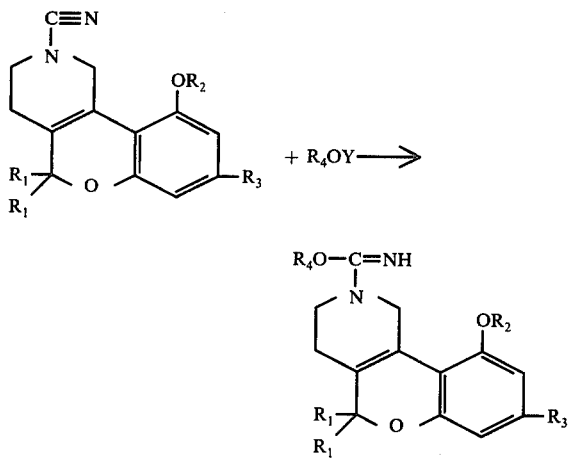

wherein $R_1$, $R_2$, $R_3$ and $R_4$ have the previously assigned significance, and Y is a reactive alkali metal such as sodium, potassium or lithium. Some of the alkali metal lower alkoxides which can be used in the process are sodium methoxide, potassium ethoxide and lithium propoxide. The reaction is readily effected in an alcohol such as methanol at ambient temperature in about 1 to 3 hours. Following termination of the reaction the desired product can be isolated from the reaction mixture by conventional procedures. In this regard, when $R_2$ is hydrogen in the starting material the phenol or hydroxy group is converted to an intermediate alkali metal salt which, however, is readily reconverted to the phenol group by use of a mild acid.

Among the lower alkyl 2-carboximidates produced as described are methyl 5,5-dimethyl-8-(1,2-dimethylheptyl)-10-hydroxy-1,2,3,4-tetrahydro-5H-[1]benzopyrano[3,4-d]pyridine-2-carboximidate, methyl 5,5-dimethyl-8(2-heptyl)-10-hydroxy-1,2,3,4-tetrahydro-5H-[1]benzopyrano[3,4-d]pyridine-2-carboximidate, ethyl 5,5-dimethyl-10-hydroxy-8-(1-pentyl)-1,2,3,4-tetrahydro-5H-[1]benzopyrano[3,4-d]pyridine-2-carboximidate, methyl 8-(1-cyclohexylethyl)-5,5-dimethyl-10-hydroxy-1,2,3,4-tetrahydro-5H-[1]benzopyrano[3,4-d]pyridine-2-carboximidate, ethyl 8-(3-cyclopentylpropyl)-5,5-dimethyl-10-hydroxy-1,2,3,4-tetrahydro-5H-[1]benzopyrano[3,4-d] pyridine-2-carboximidate, propyl 5,5-dimethyl-8-[4-(4-fluorophenyl)-1-methylbutyl]-10-hydroxy-1,2,3,4-tetrahydro-5H-[1]benzopyrano[3,4-d]pyridine-2-carboximidate, methyl 5,5-dimethyl-8-[4-(4-methylphenyl)-1-methylbutyl]-10-hydroxy-1,2,3,4-tetrahydro-5H-[1]benzopyrano[3,4-d]pyridine-2-carboximidate and ethyl 5,5-dimethyl-8-(1,2-dimethyl-7-phenylheptyl)-10-hydroxy-1,2,3,4-tetrahydro-5H-[1]benzopyrano [3,4-d]pyridine-2-carboximidate and the corresponding compounds in which a 10-methoxy, ethoxy, propoxy, butoxy and pentoxy group is present in place of the 10-hydroxy group.

In all of the compounds named previously in this specification the 5,5-dimethyl substituents can be replaced with 5,5-diethyl, 5,5-dipropyl and other lower alkyl groups to the extent such substitution is not prevented by steric hindrance.

The compounds of this invention, having a basic nitrogen atom, readily form acid addition salts with inorganic acids and organic acids such as hydrochloric acid, sulfuric acid, phosphoric acid, citric acid, acetic acid, maleic acid and oxalic acid.

The compounds of this invention, as a base or non-toxic acid addition salt, in which R is carboxamidoxime or is a carboximidate group and $R_2$ is hydrogen or lower alkyl, when administered to a mammal parenterally or orally exert an anti-hypertensive effect. The compounds thus can be used to reduce blood pressure.

5,5-dimethyl-8-(1,2-dimethylheptyl)-10-hydroxy-1,2,3,4-tetrahydro-5H-[1]benzopyrano[3,4-d]pyridine-2-carboxamidoxime administered intraperitoneally to anesthetized hypertensive rats at 10 and 20 mg/kg lowered the mean arterial blood pressure about 46 to 60% in the first one-half hour after administration and the blood pressure remained depressed for at least 2 hours. The same compound at 10 and 20 mg/kg administered intraperitoneally to unanesthetized hypertensive rats lowered systolic blood pressure 16 to 39% in about 2 hours. A 10 mg/kg dose of the compound in unanesthetized normotensive rats lowered the systolic blood pressure about 25% in about 2.25 hours.

5,5-dimethyl-8-(1,2-dimethylheptyl)-10-methoxy-1,2,3,4-tetrahydro-5H-[1]benzopyrano[3,4-d]pyridine-2-carboxamidoxime administered intraperitoneally to anesthetized hypertensive rats at doses of 1 to 17 mg/kg lowered the mean arterial blood pressure 33 to 68% in thirty to forty-five minutes or less. The same compound at 5 to 20 mg/kg administered intraperitoneally to unanesthetized hypertensive rats lowered systolic blood pressure 14 to 68% in one-half hour to one hour or less. Dosages of 1 to 10 mg/kg intraperitoneally of the compound in anesthetized normotensive rats lowered the mean arterial blood pressure about 30 to 67% in one-half hour to two hours.

Methyl 5,5-dimethyl-8-(1,2-dimethylheptyl)-10-methoxy-1,2,3,4-tetrahydro-5H-[1]benzopyrano[3,4-d]pyridine-2-carboximidate at dosages of 0.5 to 10 mg/kg intraperitoneally in unanesthetized normotensive rats lowered systolic blood pressure 10 to 32% in less than one-half hour with dosages of 2 mg/kg and less and giving results as good as higher dosages.

The amount of active ingredient administered may be varied; however, it is necessary that the amount of active ingredient be such that a suitable dosage is given. The selected dosage depends upon the desired therapeutic effect and on the duration of treatment. Dosages of from 0.01 to 25 mg/kg of body weight daily, preferably in divided doses, i.e., three to four times daily, can be administered.

The active agents of this invention can be administered to animals, including humans, as pure compounds. It is advisable, however, to first combine one or more of the compounds with a suitable pharmaceutical carrier to attain a satisfactory size to dosage relationship and thereby obtain a pharmaceutical composition.

Pharmaceutical carriers which are liquid or solid can be used. Solid carriers such as starch, sugar, talc and the like can be used to form powders. The powders can be used for direct administration or they may be used to make tablets or to fill gelatin capsules. Suitable lubricants like magnesium stearate, binders such as gelatin, and disintegrating agents like sodium carbonate in combination with citric acid can be used to form tablets. Sweetening and flavoring agents can also be included.

Unit dosage forms such as tablets and capsules can contain any suitable predetermined amount of one or more of the active agents, and they may be administered one or more at a time at regular intervals. Such unit dosage forms, however, should generally contain a concentration of 0.1 to 50 percent by weight of one or more of the active compounds. Unit dosage forms, such as tablets and capsules, can contain about 2 to 300 mg of active agent.

A typical tablet can have the composition:

|  | Mg |
| --- | --- |
| Active agent (1) | 100 |
| Starch U.S.P. | 57 |
| Lactose U.S.P. | 73 |
| Talc, U.S.P. | 9 |
| Stearic acid | 12 |

(1) 5,5-dimethyl-8-(1,2-dimethylheptyl)-10-hydroxy-1,2,3,4-tetrahydro-5H-[1]benzopyrano[3,4-d]pyridine-2-carboxamidoxime The compounds exhibit both oral and parenteral activity and accordingly they can be formulated in dosage forms for either oral or parenteral administration to a patient.

Solid dosage forms for oral administration include capsules, tablets, pills, powders, granules and the like.

Liquid dosage forms for oral administration include emulsions, solutions, suspensions, syrups and the like, containing diluents commonly used in the art, such as water. Besides inert diluents, such preparations can also include adjuvants such as wetting agents, emulsifying and suspending agents and sweetening, flavoring and perfuming agents.

Preparations for parenteral administration include sterile aqueous or non-aqueous solutions. Examples of non-aqueous solvents or vehicles are propylene glycol, polyethylene glycol, vegetable oils such as olive oil and injectable organic esters such as ethyl oleate. The parenteral preparations are sterilized by conventional methods.

The following examples are presented to further illustrate the invention.

EXAMPLE 1

2-Cyano-5,5-dimethyl-8-(1,2-dimethylheptyl)-10-hydroxy-1,2,3,4-tetrahydro-5H-[1]benzopyrano[3,4-d]pyridine A mixture of 4.6 g (0.0129 mole) of 5,5-dimethyl-8-(1,2-dimethylheptyl)-10-hydroxy-1,2,3,4-tetrahydro-5H-[1] benzopyrano[3,4-d]pyridine, 1.38 g (0.013 mole) of cyanogen bromide, 2.13 g (0.026 mole) of sodium acetate and 35 ml of methanol was stirred at 0° C for 3 hours, and then at ambient temperature for 12 hours. After removal of the solvent under reduced pressure, water was added to the residue and the mixture was extracted with diethyl ether. The organic layer was washed with 2 N HCl, followed by saturated NaCl solution. The ether layer was separated, dried over $Na_2SO_4$ and concentrated to give 2-cyano-5,5-dimethyl-8-(1,2-dimethylheptyl)-10-hydroxy-1,2,3,4-tetrahydro-5H-[1]benzopyrano[3,4-d]pyridine as a yellow oil (4.9 g, 99% yield) which crystallized upon standing.

Anal. Calcd. for $C_{24}H_{34}N_2O_2$: C, 75.35; H, 8.96; N, 7.32. Found: C, 75.19; H, 8,89; N, 7.14.

EXAMPLE 2

5,5-Dimethyl-8-(1,2-dimethylheptyl)-10-hydroxy-1,2,3,4-tetrahydro-5H-[1]benzopyrano[3,4-d]pyridine-2-carboxamidoxime A mixture of 0.5 g (1.31 mmole) of 2-cyano-5,5-dimethyl-8-(1,2-dimethylheptyl)-10-hydroxy-1,2,3,4-tetrahydro-5H-[1]benzopyrano[3,4-d]pyridine, 0.139 g (2.0 mmole) of hydroxylamine hydrochloride and 0.212 g (2.0 mmole) of sodium carbonate in 17 ml of dimethylformamide was heated on a steam bath for 1.5 hours. After cooling, the reaction mixture was partitioned between 50 ml each of chloroform and water. The organic layer was separated, washed with water, dried over $Na_2SO_4$ and filtered. After removal of the solvents on a rotary evaporator, the last traces of dimethylformamide were removed in vacuo. Crystallization from chloroform gave 280 mg (56%) of 5,5-dimethyl-8-(1,2-dimethylheptyl)-10-hydroxy-1,2,3,4-tetrahydro-5H-[1]benzopyrano[3,4-d]pyridine-2-carboxamidoxime as colorless crystals. Recrystallization of the compound from chloroform gave poor recovery (17.5%) of the crystalline material, m.p. 142°–45° C. The assigned structure was confirmed by the ir, nmr and mass spectra ($M^+$ at 415). Thin-layer chromatography (20% methanol/chloroform on silica gel) revealed two spots corresponding to the two stereoisomers.

EXAMPLE 3

2-Cyano-5,5-dimethyl-8-(1,2-dimethylheptyl)-10-methoxy-1,2,3,4-tetrahydro-5H-[1]benzopyrano[3,4-d]pyridine A mixture of 2.3 g (0.006 mole) of 2-cyano-5,5-dimethyl-8-(1,2-dimethylheptyl)-10-hydroxy-1,2,3,4-tetrahydro-5H-[1]benzopyrano[3,4-d]pyridine, 2.8 g (0.02 mole) of iodomethane and 10 g (0.0725 mole) of potassium carbonate in anhydrous acetone was heated at reflux, with stirring, for 7 hours. After cooling, the solid was removed by filtration and discarded, and the mother liquor was concentrated on a rotary evaporator. The residual material was taken up in diethyl ether (70 ml) and washed with water, 1N HCl, and again with water. The organic layer was dried over sodium sulfate, filtered and concentrated to give 1.84 g (78%) of 2-cyano-5,5-dimethyl-8-(1,2-dimethylheptyl)-10-methoxy-1,2,3,4-tetrahydro-5H-[1]benzopyrano[3,4-d]pyridine as a yellow oil. The ir and nmr spectra confirmed the structure. The compound appeared pure by thin-layer chromatography (silica gel, chloroform solvent system).

EXAMPLE 4

5,5-Dimethyl-8-(1,2-dimethylheptyl)-10-methoxy-1,2,3,4-tetrahydro-5H-[1]benzopyrano[3,4-d]pyridine-2-carboxamidoxime A mixture of 238 mg (0.6 mmole) of 2-cyano-5,5-dimethyl-8-(1,2-dimethylheptyl)-10-methoxy-1,2,3,4-tetrahydro-5H-[1]benzopyrano[3,4-d]pyridine, 69.5 mg (1.0 mmole) of hydroxylamine hydrochloride and 106 mg (1.0 mmole) of sodium carbonate in 7 ml of dimethylformamide was heated on a steam bath for 2.5 hours. The progress of the reaction was monitored by tlc (silica gel, 5% $MeOH/CHCl_3$). After cooling, 70 ml of chloroform was added and the mixture was extracted with water (2 × 75 ml). The organic layer was separated, dried over $Na_2SO_4$, filtered and concentrated to give a residue which crystallized from chloroform/hexane to give 120 mg (47%) of colorless solid 5,5-dimethyl-8-(1,2-dimethylheptyl)-10-methoxy-1,2,3,4-tetrahydro-5H-[1]benzopyrano[3,4-d]pyridine-2-carboxamidoxime, m.p. 173°–76° C. The ir, nmr and mass spectra (M+ at 429) confirmed the structure. The reaction was repeated on a larger scale to give 18% of the desired product, m.p. 176°–78° C.

Anal. Calcd. for $C_{25}H_{39}N_3O_3$: C, 69.93; H, 9.09; N, 9.79. Found: C, 69.61; H, 9.16; N, 9.75.

EXAMPLE 5

Methyl 5,5-Dimethyl-8-(1,2-dimethylheptyl)-10-methoxy-1,2,3,4-tetrahydro-5H-[1]benzopyrano[3,4-d]pyridine-2-carboximidate A mixture of 198 mg (0.5 mmole) of 2-cyano-5,5-dimethyl-8-(1,2-dimethylheptyl)-10-methoxy-1,2,3,4-tetrahydro-5H-[1]benzopyrano[3,4-d]pyridine and 2.7 mg (0.05 mmole) of sodium methoxide in 8 ml of methanol was refluxed with stirring for 3 hours and allowed to stir overnight at ambient temperature. Ammonium chloride (29.4 mg; 0.55 mmole) was added and the stirring was continued for an additional 2 hours. The reaction mixture was concentrated on a rotary evaporator to give a residue to which was added 1 ml of diethyl ether. The solid was collected by filtration to give 138 mg in two crops (59%) of methyl 5,5-dimethyl-8-(1,2-dimethylheptyl)-10-methoxy-1,2,3,4-tetrahydro-5H-[1]benzopyrano[3,4-d]pyridine-2-carboximidate as a light yellow solid, m.p. 134°–36° C. The ir and nmr spectra confirmed the structure.

Anal. Calcd. for $C_{26}H_{40}N_2O_3 \cdot CH_3OH$: C, 70.40; H, 9.62; N, 6.08. Found: C, 70.82; H, 9.12; N, 6.16.

The foregoing detailed description has been given for clearness of understanding only, and no unnecessary limitations should be understood therefrom, as modifications will be obvious to those skilled in the art.

What is claimed is:

1. A compound of the formula

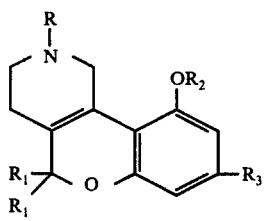

wherein R represents —C≡N,

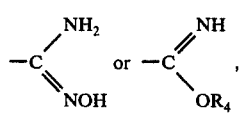

$R_1$ is lower alkyl, $R_2$ is hydrogen or lower alkyl and $R_3$ is straight or branched alkyl of 1 to 20 carbons, cycloalkyl-lower alkyl in which the cycloalkyl has 3 to 8 carbons or it is phenyl-alkyl in which the alkyl has 1 to 10 carbons and $R_4$ is lower alkyl, and nontoxic acid addition salts thereof.

2. A compound according to claim 1 in which R is —C≡N.

3. A compound according to claim 1 in which R is

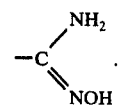

4. A compound according to claim 1 in which R is

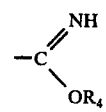

and $R_4$ is lower alkyl group.

5. A compound according to claim 2 in which $R_1$ is methyl.

6. A compound according to claim 3 in which $R_1$ is methyl.

7. A compound according to claim 5 in which $R_2$ is hydrogen or methyl.

8. A compound according to claim 6 in which $R_2$ is hydrogen or methyl.

9. A compound according to claim 4 in which R is

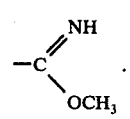

10. A compound according to claim 9 in which $R_1$ is methyl.

11. A compound according to claim 10 in which $R_2$ is hydrogen or methyl.

12. A compound according to claim 1 named 2-cyano-5,5-dimethyl-8-(1,2-dimethylheptyl)-10-hydroxy-1,2,3,4-tetrahydro-5H-[1]benzopyrano[3,4-d]pyridine.

13. A compound according to claim 1 named 2-cyano-5,5-dimethyl-8-(1,2-dimethylheptyl)-10-methoxy-1,2,3,4-tetrahydro-5H-[1]benzopyrano[3,4-d]pyridine.

14. A compound according to claim 1 named 5,5-dimethyl-8-(1,2-dimethylheptyl)-10-hydroxy-1,2,3,4-tetrahydro-5H-[1]benzopyrano[3,4-d]pyridine-2-carboxamidoxime.

15. A compound according to claim 1 named 5,5-dimethyl-8-(1,2-dimethylheptyl)-10-methoxy-1,2,3,4-tetrahydro-5H-[1]benzopyrano[3,4-d]pyridine-2-carboxamidoxime.

16. A compound according to claim 1 named methyl 5,5-dimethyl-8-(1,2-dimethylheptyl)-10-methoxy-1,2,3,4-tetrahydro-5H-[1]benzopyrano[3,4-d]pyridine-2-carboximidate.

17. A pharmaceutical composition for lowering blood pressure containing as an active ingredient a therapeutically effective compound of claim 1, and a pharmaceutically acceptable carrier.

18. A method of lowering blood pressure in an animal which comprises administering a safe but effective amount of a compound of claim 1 to the animal.

* * * * *